(12) United States Patent
Santos et al.

(10) Patent No.: US 7,101,572 B2
(45) Date of Patent: Sep. 5, 2006

(54) TASTE MASKED AQUEOUS LIQUID PHARMACEUTICAL COMPOSITION

(75) Inventors: Joyce Bedelia B. Santos, Mandaluyong (PH); Rita Josefina M. Santos, Quezon (PH); Kennie U. Dee, Quezon (PH)

(73) Assignee: Unilab Pharmatech, Ltd., Central Hong Kong (CN)

( * ) Notice: Subject to any disclaimer, the term of this patent is extended or adjusted under 35 U.S.C. 154(b) by 638 days.

(21) Appl. No.: 10/017,697

(22) Filed: Dec. 7, 2001

(65) Prior Publication Data

US 2003/0118654 A1   Jun. 26, 2003

(51) Int. Cl.
- A61K 31/43 (2006.01)
- A61K 31/545 (2006.01)
- A61K 31/4965 (2006.01)
- A61K 31/522 (2006.01)
- A61K 31/44 (2006.01)

(52) U.S. Cl. ............. 424/486; 514/192; 514/200; 514/255.04; 514/263.34; 514/282; 514/290; 514/629; 514/649

(58) Field of Classification Search ........... 424/484, 424/498, 486; 514/192, 200, 255.04, 263.34, 514/282, 290, 629, 649
See application file for complete search history.

(56) References Cited

U.S. PATENT DOCUMENTS

| | | | |
|---|---|---|---|
| 4,623,537 A | 11/1986 | Kearns | 424/49 |
| 5,154,926 A | 10/1992 | Kawasaki et al. | 424/439 |
| 5,431,916 A * | 7/1995 | White | 424/451 |
| 5,563,177 A | 10/1996 | Popli et al. | 514/718 |
| 5,602,182 A | 2/1997 | Popli et al. | 514/653 |
| 5,616,621 A | 4/1997 | Popli et al. | 514/772.4 |
| 5,658,919 A | 8/1997 | Ratnaraj et al. | 514/269 |
| 5,763,449 A | 6/1998 | Anaebonam et al. | 514/275 |
| 5,962,461 A | 10/1999 | Anaebonam et al. | 514/275 |

FOREIGN PATENT DOCUMENTS

| EP | 1025858 A1 | 8/2000 |
|---|---|---|
| WO | WO 95/00133 | 1/1995 |

OTHER PUBLICATIONS

Buhler, Volker, "Kollidon Polyvinylpyrrolidone for the Pharmaceutical Industry", Mar. 1998, pp. 39-42, 113-119, 179-182 4th Edition, BASF.

Higuchi, Takeru and Kristiansen, Harold, "Blinding Specificity Between Small Organic Solutes in Aqueous Solution: Classification of Some Solutes into Two Groups According to Binding Tendencies", Journal of Pharmaceutical Sciences, pp. 1601-1607, vol. 59, No. 11 Nov. 1970.

Horn, D and Ditter, W, "Chromatographic Study of Interactions Between Polyvinlypyrrolidone and Drugs", Journal of Pharmaceutical Sciences, pp. 1021-1026, vol. 71, No. 9, Sep. 1982.

Remington's Pharmaceutical Sciences, 18th Edition 1990, "Flavoring Agents", pp. 1290-1292, Mack Publishing Company.

* cited by examiner

Primary Examiner—Michael G. Hartley
Assistant Examiner—Blessing Fubara
(74) Attorney, Agent, or Firm—Thomas T. Aquilla

(57) ABSTRACT

A substantially taste masked liquid pharmaceutical composition containing a pharmaceutically effective amount of an unpleasant tasting drug dissolved or dispersed in an aqueous excipient base, said excipient base comprising polyvinyl pyrrolidone and/or copolyvidone, and high molecular weight polyethylene glycol.

46 Claims, No Drawings

TASTE MASKED AQUEOUS LIQUID PHARMACEUTICAL COMPOSITION

BACKGROUND OF THE INVENTION

1. Field of the Invention

The present invention relates to a liquid drug composition, and more particularly to a substantially taste masked aqueous liquid pharmaceutical composition that contains an otherwise unpleasant tasting drug.

2. Description of Related Art

The most convenient and commonly employed route of drug delivery has been by oral ingestion, either in liquid or solid formats. The unpalatable taste of most drugs is generally not a problem with solid dosage formats, which are intended to be swallowed whole. In the case of capsules, the hard gelatin shell prevents the drug from being tasted during the short transit time in the mouth. Tablets, on the other hand, can be coated with sugar or film forming polymers for tastemasking.

Many children and some adults however have difficulty swallowing solid dosage formats, and in this case, the drug is given in liquid form, either as syrup or suspension. Most drugs however are bitter, and this can lead to poor patient compliance. Because the threshold for bitterness is low, only a very small amount of dissolved drug is needed for perception of bitterness.

The prior art has shown extensive use of one or a combination of different flavoring methodologies to mask the bitter taste of drugs. For example, a flavor can be selected that complements the taste of the preparation, or a flavor with a longer intensity and stronger taste than the drug can be used. High levels of sweetening agents are often used to overwhelm bitterness with sweetness. The taste buds may also be anesthetized by menthol or mint flavors. These approaches are generally not very effective in masking the taste of a bitter drug, and a flavoring system that works with one drug usually does not apply to another drug.

The prior art also indicates that taste masking could also be achieved by increasing the viscosity of liquid preparations. Various combinations of viscosity modifiers for taste masking exist in the patent literature. For example, U.S. Pat. No. 5,616,621 provides taste masked liquid preparations by increasing the viscosity with a combination of polyethylene glycol and sodium carboxymethylcellulose; U.S. Pat. No. 5,658,919 discloses taste masking of acetaminophen suspension using a suspending system consisting of xanthan gum and a mixture of cellulosic polymers. The increase in viscosity is assumed to limit the contact of the drug with the tongue, presumably by slowing down salivary water uptake into the viscous liquid medicament, which can lead to dilution and dissolution of the ingested medication. This approach is only moderately successful in reducing bitterness especially at high drug loading. While bitterness may be reduced at the onset, bitter aftertaste becomes prominent after swallowing because thick preparations are more difficult to wash down thus leaving behind some residual viscous liquid medicament in the mouth after swallowing. This bitter aftertaste is more prominent with water intake due to the reduction in viscosity and dilution of the residual liquid medicament and subsequent dissolution of the drug in the mouth.

Several other approaches have been pursued to address the unpleasant taste of a drug in a liquid format. U.S. Pat. No. 5,730,997 illustrates the use of a hyperosmotic liquid using a sugar derivative and maltose syrup for taste masking. U.S. Pat. No. 5,154,926 claims reduction of the bitter taste of acetaminophen syrup by using a water-soluble macromolecule with a polyhydric alcohol and/or polymer of a polyhydric alcohol of MW 300–400. U.S. Pat. Nos. 5,763,449 and 5,962,461 teach the use of a combination of povidone, C3–C6 polyol and ammonium glycyrrhizinate for taste masking. EP application 1025858 A1 discloses relief of bitterness of basic drugs by combining propylene glycol with povidone and/or copolyvidone.

The disclosure that follows illustrates another, more general solution to the problem of bad taste in liquid compositions containing either dissolved or dispersed drugs.

SUMMARY OF THE INVENTION

The present invention provides a taste masked oral liquid composition comprising at least one therapeutically effective amount of a bitter-tasting drug. The drug is dissolved or dispersed in an aqueous taste masking excipient base comprising a high molecular weight (MW) polyethylene glycol, a polyvinyl pyrrolidone and/or copolyvidone. The taste masked liquid composition has substantially reduced bitter taste and aftertaste.

In preferred embodiments of the invention, the oral pharmaceutical liquid composition comprises about 0.1 to about 10 weight percent of at least one bitter-tasting drug wherein the bitter-tasting drug is an aromatic compound with hydrophilic groups that can form hydrogen bonds such as hydroxyl, carboxylic or amine groups; about 0.5 to about 10 weight percent of polyvinyl pyrrolidone and/or copolyvidone; about 0.05 to about 10 weight percent polyethylene glycol of MW 4000–6000; about 30–90% of a sweetening composition; about 0 to 0.4% of a viscosity-building agent; about 0–20% of a polyhydric alcohol, and 0.1–0.5% of a flavoring agent. The liquid composition is adjusted to a pH between 2.5 to 8.

DETAILED DESCRIPTION OF THE INVENTION

The present invention contemplates a taste masked liquid composition where the liquid composition is a syrup, a ready-to-use suspension, or extemporaneously prepared liquid syrup or suspension such as, for example, dry powder for reconstitution with water, liquid concentrate for dilution, dispersible tablet or capsule. In the case of extemporaneously prepared syrup or suspension, the concentration of ingredients are based on the reconstituted product.

The liquid pharmaceutical composition of the present invention contains at least one normally bitter tasting drug as active ingredient. The bitter-tasting drugs are present at therapeutically effective amounts in the dosage form. These amounts differ depending on the drug and prescribed dosage regimens. For instance, liquid preparations intended for infants generally contain high drug concentrations to enable small doses and reduced dosing frequency. The amount of drug in the composition is from about 0.02 to about 15 percent by weight, preferably from about 0.1 to about 10 percent by weight of the total composition. In the case of dry powder for reconstitution with water, the drug may be present as uncoated or coated particles. Coated drug particles are not usually perfectly sealed. After reconstitution, some amount of drug can leach out through the coating into the liquid phase during storage, which can result in some bitterness in the product.

Bitter tasting drugs that may be used with the liquid composition are aromatic compounds with hydrophilic groups that can form hydrogen bonds such as hydroxyl, carboxylic or amine groups. These drugs may be selected from but not limited to the group consisting of analgesics, decongestants, antitussives, expectorants, antihistamines, mucolytics, laxatives, vasodilators, anti-arrhythmics, anti-diarrhea drugs, anti-hypertensives, antibiotics, narcotics, bronchodilators, anti-inflammatory drugs, cardiovascular drugs, tranquilizers, antipsychotics, antitumor drugs, sedatives, antiemetics, anti-nauseants, anti-convulsant, neuromuscular drugs, hypoglycemic agents, diuretics, antispasmodics, uterine relaxants, antiobesity drugs, antianginal drugs, and antiviral drugs. Combinations of these drugs can also be used.

Particular unpleasant tasting drugs include but are not limited to acetaminophen, ibuprofen, phenylpropanolamine hydrochloride, pseudoephedrine hydrochloride, phenylephrine hydrochloride, diphenhydramine hydrochloride, guaifenesin, dextromethorphan hydrobromide, chlorpheniramine maleate, brompheniramine maleate, terfenadine, loratadine, descarboethoxyloratadine, bromhexine hydrochloride, ambroxol hydrochloride, salbutamol sulphate, amoxicillin, ampicillin, cloxacillin, flucloxacillin, cephalexin, and combinations thereof.

One embodiment of the present invention contains acetaminophen from about 1 to about 15 weight percent, preferably from about 2 to about 10 weight percent of total composition. A second embodiment of the invention contains guaifenesin from about 0.5 to about 10 weight percent, preferably from about 1 to about 5 weight percent of total composition. If suspensions of these drugs are to be prepared, the drug should preferably be micronized with more than 80% of the particles having a particle size less than or equal to 10 microns and not more than 15% having particle sizes greater than or equal to 50 microns.

In the present invention, the normally bitter drug is dissolved or dispersed in an aqueous taste masking excipient base comprising a polyvinyl pyrrolidone and/or copolyvidone, and a high MW polyethylene glycol. The taste masked liquid composition has substantially reduced bitter taste and aftertaste.

A contemplated composition contains about 0.1 to about 30 weight percent polyvinyl pyrrolidone (PVP) and/or copolyvidone, preferably about 0.5 to about 10 weight percent, more preferably about 1 to about 7 weight percent of total composition. The PVP can either be water-soluble or water-insoluble. PVP is commercially available from a number of suppliers. The water-soluble PVPs or povidone sold under the Trademark KOLLIDON K25, K30, K90 having molecular weights of 28,000–34,000, 44,000–54,000, and 1,000,000–1,500,000, respectively, are preferred for use, with the K25 and K30 being most preferred. Water-insoluble PVPs referred to as crospovidone or crospolyvidone are crosslinked insoluble polyvinyl pyrrolidone. Crospovidone is available from BASF under the Trademark KOLLIDON CL, KOLLIDON CL-M, CROSPOVIDONE M. Copolyvidone is a copolymer of vinyl pyrrolidone and vinyl acetate available from BASF under the Tradename KOLLIDON VA 64. In the present invention, water-soluble PVPs, water-insoluble PVPs, and copolyvidone may be used either singly or in combination.

The disclosure of Volker Bühler's book, Kollidon, BASF Aktiengesellschaft, Ludwigshafen, Germany (1992) teaches the use of PVP as both a solubilization aid for several drugs as well as for specifically masking the bitter taste of acetaminophen. This book teaches that PVP forms complexes with aromatic compounds particularly those with hydrophilic groups that can form hydrogen bonds such as hydroxyl, carboxyl, and amine groups. See also Horn et al., J. Pharm. Sci., 71:1021–126 (1982). It is thought that PVP forms a complex with acetaminophen reducing its bitter taste. An exemplary formulation for an oral liquid PVP- and acetaminophen syrup composition is provided in page 113, Table 81 of the above Bühler's text. This formulation contains 5 weight percent of fully dissolved acetaminophen and 20 weight percent Kollidon K25.

Consistent with Bühler's disclosure, we have found that the addition of PVP improves the taste of an acetaminophen suspension. The bitterness reduction however is still not significant to eliminate the bitterness especially the bitter aftertaste.

We have now surprisingly found that the bitterness of an acetaminophen suspension especially the bitter aftertaste can be significantly improved by using a high molecular weight polyethylene glycol (PEG) with PVP and/or copolyvidone. This despite the fact that polyethylene glycol is known to increase the solubility of acetaminophen.

Thus, the amount of dissolved acetaminophen would have been theoretically higher when polyethylene glycol is used with PVP and/or copolyvidone in an acetaminophen suspension, which in turn should have increased the bitterness, and yet on contrary, significant reduction in bitterness especially on the bitter aftertaste was achieved. The improvement is more prominent when water intake follows swallowing of the medication. The molecular weight of polyethylene glycol is critical to its contribution to taste masking when combined with PVP and/or copolyvidone. Liquid polyethylene glycol with MW 400–600 has no effect on tastemasking, only the semisolid/solid polyethylene glycol of MW$\geq$900 works. The higher the molecular weight, the lower the level of polyethylene glycol required. The preferred polyethylene glycol molecular weight is about 2000 to about 8000, more preferably the molecular weight is about 4000 to about 6000. The amount of polyethylene glycol is from about 0.01 to about 25 weight percent, preferably from about 0.05 to about 10 weight percent, and more preferably from about 0.1 to about 5 weight percent.

We have also surprisingly found that the taste masking effect of high molecular weight polyethylene glycol and PVP and/or copolyvidone are not limited to suspensions but also to fully dissolved drugs (syrups) such as for example Guaifenesin or lower levels of acetaminophen. The mechanism by which debittering is achieved is unknown. However, without wishing to be bound by theory, it is believed that a complex is formed between the drug and PVP and/or copolyvidone, with the high molecular weight polyethylene glycol potentiating debittering by competing with unbound drug for taste receptors of bitterness.

The taste masked liquid composition of the present invention may contain additional ingredients used in the drug industry, herein referred to as additives. Additives include well-known components, but are not limited to sweetening agents, flavors, colorants, antioxidants, chelating agents, viscosity-building agents, surfactants, pH modifiers, bulking agents, acidifiers, cosolvents, and mixtures thereof.

Representative sweetening agents include but not limited to:

(1) Water-soluble sweetening agents such as monosaccharides, disaccharides, sugar alcohols, and polysaccharides, e.g., glucose, fructose, invert sugar, sorbitol, sucrose, maltose, xylose, ribose, mannose, corn syrup solids, xylitol, mannitol, maltodextrins, and mixtures thereof. In general, water-soluble sweetening agents selected from sugar, invert sugar, sorbitol, mannitol, and mixtures thereof are useful at amounts of about 20 to about 95 weight percent, with amounts of about 30 to about 90 weight percent being preferred, and about 40 to about 85 weight percent being more preferred.

(2) Water-soluble artificial sweeteners and dipeptide-based sweeteners such as saccharin salts, acesulfame-K, sucralose, aspartame, and mixtures thereof. In general, these sweeteners are used in combination with water-soluble sweetening agents to enhance sweetness.

Flavors that may optionally be added to the taste masked liquid excipient base of the present invention are those known in the pharmaceutical art. For example, synthetic flavor oils, and/or naturally derived oils from plants, flowers, leaves, and so forth, and combinations thereof are useful. In general, amounts of about 0.05 to about 5 weight percent of the total composition are useful with amounts of about 0.1 to about 1.5 weight percent being preferred and about 0.2 to about 1 weight percent being most preferred.

The taste masked liquid composition of the present invention may optionally contain viscosity-building agents from 0 to about 7 weight percent of total composition, preferably from about 0.05 to about 5 weight percent, and most preferably from about 0.1 to about 3 weight percent. The viscosity-building agents may be selected from but not limited to xanthan gum, carrageenan, tragacanth, guar gum, pectin, carboxymethylcellulose, hydroxypropyl methylcellulose, hydroxypropylcellulose, methylcellulose, microcrystalline cellulose and carboxymethylcellulose sodium blends, and mixtures thereof. The viscosity-building agent provides both body and mouthfeel to the preparation. The viscosity-building agent must be selected carefully to ensure compatibility with the drug and the other components of the formulations.

A cosolvent may optionally be used to dissolve or rapidly disperse additives, or as a solubilizer for the drugs. Ethanol and polyhydric alcohols such as glycerin, propylene glycol, low molecular weight polyethylene glycols, and mixtures thereof are generally employed as cosolvents.

In the case of dry powders for reconstitution, the powders or granules may optionally contain anti-caking agents to improve the flow properties of dry powders during processing and prevent the powders from caking during storage. The anti-caking agents may be selected from but not limited to colloidal silicon dioxide, tribasic calcium phosphate, powdered cellulose, magnesium trisilicate, starch, and mixtures thereof.

The invention will now be described with respect to the following specific examples.

Experiment 1

The effective amount of crospovidone needed to reduce the bitterness of a liquid suspension containing acetaminophen was determined by evaluating compositions containing 0, 2.5%, 5% and 10% crospovidone.

TABLE 1

Acetaminophen Suspension

| Ingredient | Example 1-A (grams per 100 ml) | Example 1-B (grams per 100 ml) | Example 1-C (grams per 100 ml) | Example 1-D (grams per 100 ml) |
|---|---|---|---|---|
| Acetaminophen | 5 | 5 | 5 | 5 |
| Xanthan gum | 0.3 | 0.3 | 0.3 | 0.3 |
| Sucrose | 55 | 55 | 55 | 55 |
| 70% Sorbitol Solution | 10 | 10 | 10 | 10 |
| Invert Sugar | 20 | 20 | 20 | 20 |
| Glycerin | 5 | 5 | 5 | 5 |

TABLE 1-continued

Acetaminophen Suspension

| Ingredient | Example 1-A (grams per 100 ml) | Example 1-B (grams per 100 ml) | Example 1-C (grams per 100 ml) | Example 1-D (grams per 100 ml) |
|---|---|---|---|---|
| Crospovidone (Kollidon CL-M) | 0 | 2.5 | 5 | 10 |
| Sodium Benzoate | 0.2 | 0.2 | 0.2 | 0.2 |
| Sorbitan Monolaurate | 0.05 | 0.05 | 0.05 | 0.05 |
| Disodium Edetate | 0.2 | 0.2 | 0.2 | 0.2 |
| Sucralose | 0.2 | 0.2 | 0.2 | 0.2 |
| Saccharin sodium | 0.13 | 0.13 | 0.13 | 0.13 |
| Coloring | 0.006 | 0.006 | 0.006 | 0.006 |
| Flavoring | 0.3 | 0.3 | 0.3 | 0.3 |
| Citric Acid | 0.1 | 0.1 | 0.1 | 0.1 |
| Sodium Citrate Dihydrate | 0.295 | 0.295 | 0.295 | 0.295 |
| Purified Water | q.s. to 100 mL | q.s. to 100 mL | q.s. to 100 mL | q.s. to 100 mL |
| pH | 5–6 | 5–6 | 5–6 | 5–6 |

The acetaminophen suspensions were prepared in the following manner:

Sucrose syrup containing sodium benzoate was prepared. The hot syrup was cooled down to 30°C. The sucrose syrup, sorbitol and invert sugar were blended together to form Phase A. Sorbitan monolaurate was added to the mixture to form Phase B. Phase B was stirred for 15 minutes.

The required amount of crospovidone (for Examples 1-B, 1-C and 1-D) was dispersed into Phase B. The admixture was stirred for 30 minutes after which acetaminophen was added. The resulting admixture was stirred for one hour to form Phase C.

Xanthan gum was dispersed in glycerin. The resulting dispersion was added to Phase C. The admixture was stirred for 15 minutes to form Phase D.

An aqueous solution of citric acid and sodium citrate dihydrate was prepared to form Phase E. An aqueous solution of disodium edetate, saccharin sodium and sucralose was prepared to form Phase F.

Phases E and F were added to Phase D. The admixture was stirred for one hour and then homogenized in a colloid mill. Color and flavor were added to the homogenized bulk, which was stirred for two more hours before adjusting to the desired volume with sugar syrup. The suspensions were allowed to stand for 24 hours before tasting.

The viscosity of the samples were determined using a Brookfield Model DV—I+ viscometer using a number 3 spindle at 30 rpm. The viscosity of samples containing 0, 2.5%, 5% and 10% crospovidone did not differ significantly from each other.

Three rounds of taste tests were done. Example 1-A was compared to Example 1-B in the first round. Example 1-B was compared to Example 1-C in round 2. Example 1-C was compared to Example 1-D in round 3. Ten respondents were asked to taste 2.5 ml of each sample in random order. The respondents were asked to drink water and take unsalted crackers between samples to remove traces of the first sample tasted. Each respondent was asked to pick a preference based on reduced bitterness. The results are presented in Tables 2, 3 and 4.

TABLE 2

| PVP (% w/v) | No. of Respondents who prefer sample |
|---|---|
| 0 | None |
| 2.5 | 10 out of 10 |

TABLE 3

| PVP (% w/v) | No. of Respondents who prefer sample |
|---|---|
| 2.5 | 2 out of 9 |
| 5 | 7 out of 9 |

TABLE 4

| PVP (% w/v) | No. of Respondents who prefer sample |
|---|---|
| 5 | 5 out of 10 |
| 10 | 5 out of 10 |

The results show that there is an optimum level of PVP required for taste masking, beyond which no further taste improvement is achieved. The taste masking effect is independent of product viscosity, which was not significantly different for the PVP range tested.

Experiment 2

The effect of adding a high molecular weight polyethylene glycol on the taste of a liquid suspension containing acetaminophen was determined by evaluating compositions containing 0, 0.5%, 2.5%, and 5% polyethylene glycol 4000.

TABLE 5

Acetaminophen Suspension

| Ingredient | Example 2-A (grams per 100 ml) | Example 2-B (grams per 100 ml) | Example 2-C (grams per 100 ml) | Example 2-D (grams per 100 ml) |
|---|---|---|---|---|
| Acetaminophen | 5 | 5 | 5 | 5 |
| Xanthan gum | 0.3 | 0.3 | 0.3 | 0.3 |
| Sucrose | 55 | 55 | 55 | 55 |
| 70% Sorbitol Solution | 10 | 10 | 10 | 10 |
| Invert Sugar | 20 | 20 | 20 | 20 |
| Glycerin | 5 | 5 | 5 | 5 |
| Polyethylene glycol (MW = 4000) | 0 | 0.5 | 2.5 | 5 |
| Sodium Benzoate | 0.2 | 0.2 | 0.2 | 0.2 |
| Sorbitan Monolaurate | 0.05 | 0.05 | 0.05 | 0.05 |
| Disodium Edetate | 0.2 | 0.2 | 0.2 | 0.2 |
| Sucralose | 0.2 | 0.2 | 0.2 | 0.2 |
| Saccharin sodium | 0.13 | 0.13 | 0.13 | 0.13 |
| Coloring | 0.006 | 0.006 | 0.006 | 0.006 |
| Flavoring | 0.3 | 0.3 | 0.3 | 0.3 |
| Citric Acid | 0.1 | 0.1 | 0.1 | 0.1 |
| Sodium Citrate Dihydrate | 0.295 | 0.295 | 0.295 | 0.295 |
| Purified Water | q.s. to 100 mL | q.s. to 100 mL | q.s. to 100 mL | q.s. to 100 mL |
| pH | 5–6 | 5–6 | 5–6 | 5–6 |

The acetaminophen suspensions were prepared in the following manner:

Sucrose syrup containing sodium benzoate was prepared. The hot syrup was cooled down to 30°C. The sucrose syrup, sorbitol and invert sugar were blended together to form Phase A. Sorbitan monolaurate was added to the mixture to form Phase B. Phase B was stirred for 15 minutes.

The required amount of polyethylene glycol (for Examples 2-B, 2-C and 2-D) was dissolved in water to form Phase C. Phase C solution was added to Phase B. The admixture was stirred for 30 minutes after which acetaminophen was added. The resulting admixture was stirred for one hour to form Phase D.

Xanthan gum was dispersed in glycerin. The resulting dispersion was added to Phase D. The admixture was stirred for 15 minutes to form Phase E.

An aqueous solution of citric acid and sodium citrate dihydrate was prepared to form Phase F. An aqueous solution of disodium edetate, saccharin sodium and sucralose was prepared to form Phase G.

Phases F and G were added to Phase E. The admixture was stirred for one hour and then homogenized in a colloid mill. Color and flavor were added to the homogenized bulk which was stirred for two more hours before adjusting to the desired volume with sugar syrup. The suspensions were allowed to stand for 24 hours before tasting.

The viscosity of the samples were determined using a Brookfield Model DV—I+ viscometer using a number 3 spindle at 30 rpm. The viscosity of samples containing 0, 0.5%, 2.5% and 5% w/v PEG did not differ significantly from each other.

Three rounds of taste tests were done comparing Example 2-A with Example 2-B, Example 2-C, and Example 2-D, respectively. Ten respondents were asked to taste 2.5 ml of each sample in random order. The respondents were asked to drink water take unsalted crackers between samples to remove traces of the first sample tasted. Each respondent was asked to pick a preference based on reduced bitterness. The results are shown in Tables 6, 7 and 8.

TABLE 6

| PEG 4000, % w/v | No. of Respondents who prefer sample |
|---|---|
| 0 | 2 |
| 0.5 | 4 out of 10 |
|  | No difference: 4 out of 10 |

TABLE 7

| PEG 4000, % w/v | No. of Respondents who prefer sample |
|---|---|
| 0 | 5 out of 10 |
| 2.5 | 5 out of 10 |

TABLE 8

| PEG 4000, % w/v | No. of Respondents who prefer sample |
|---|---|
| 0 | None |
| 5 | 10/10 |

Results show that a minimum amount of polyethylene glycol is required to achieve significant taste improvement. When used singly for taste masking, amounts of about 2.5 to about 5% w/v high molecular weight polyethylene glycol were found to be effective. These amounts in typical formulations, however, exceed acceptable daily intake levels, thus limiting the use of polyethylene glycol singly to achieve taste masking.

Experiment 3

The effect of combining crospovidone and high molecular weight polyethylene glycol on the taste of a liquid suspension containing acetaminophen was determined. The taste of a sample containing crospovidone and polyethylene glycol 4000 was compared with a sample containing only crospovidone, and a sample containing only polyethylene glycol 4000, respectively.

TABLE 9

Acetaminophen Suspension

| Ingredient | Example 3-A (grams per 100 ml) | Example 3-B (grams per 100 ml) | Example 3-C (grams per 100 ml) |
| --- | --- | --- | --- |
| Acetaminophen | 5 | 5 | 5 |
| Xanthan gum | 0.3 | 0.3 | 0.3 |
| Sucrose | 55 | 55 | 55 |
| 70% Sorbitol Solution | 10 | 10 | 10 |
| Invert Sugar | 20 | 20 | 20 |
| Glycerin | 5 | 5 | 5 |
| Polyethylene glycol (MW = 4000) | 0 | 0.5 | 0.5 |
| Crospovidone (Kollidon CL-M) | 5 | 0 | 5 |
| Sodium Benzoate | 0.2 | 0.2 | 0.2 |
| Sorbitan Monolaurate | 0.05 | 0.05 | 0.05 |
| Disodium Edetate | 0.2 | 0.2 | 0.2 |
| Sucralose | 0.2 | 0.2 | 0.2 |
| Saccharin sodium | 0.13 | 0.13 | 0.13 |
| Coloring | 0.006 | 0.006 | 0.006 |
| Flavoring | 0.3 | 0.3 | 0.3 |
| Citric Acid | 0.1 | 0.1 | 0.1 |
| Sodium Citrate Dihydrate | 0.295 | 0.295 | 0.295 |
| Purified Water | q.s. to 100 mL | q.s. to 100 mL | q.s. to 100 mL |
| pH | 5–6 | 5–6 | 5–6 |

The acetaminophen suspensions were prepared in the following manner:

Sucrose syrup containing sodium benzoate was prepared. The hot syrup was cooled down to 30□C. The sucrose syrup, sorbitol and invert sugar were blended together to form Phase A. Sorbitan monolaurate was added to the mixture to form Phase B. Phase B was stirred for 15 minutes.

The required amount of polyethylene glycol (for Examples 3-B and 3-C) was dissolved in water to form Phase C. Phase C solution was added to Phase B. The required amount of crospovidone (for Examples 3-A and 3-C) was added to Phase B. The admixture was stirred for 30 minutes after which acetaminophen was added. The resulting admixture was stirred for one hour to form Phase D.

Xanthan gum was dispersed in glycerin. The resulting dispersion was added to Phase D. The admixture was stirred for 15 minutes to form Phase E.

An aqueous solution of citric acid and sodium citrate dihydrate was prepared to form Phase F. An aqueous solution of disodium edetate, saccharin sodium and sucralose was prepared to form Phase G.

Phases F and G were added to Phase E. The admixture was stirred for one hour and then homogenized in a colloid mill. Color and flavor were added to the homogenized bulk which was stirred for two more hours before adjusting to the desired volume with sugar syrup. The suspensions were allowed to stand for 24 hours before tasting.

Two rounds of taste tests were done comparing Example 3-C with Example 3-A, and Example 3-C with Example 3-B, respectively. Eleven respondents were asked to taste 2.5 ml of each sample in random order. The respondents were asked to drink water and take unsalted crackers between samples to remove traces of the first sample tasted. Each respondent was asked to pick a preference based on reduced bitterness.

The formulation containing crospovidone and polyethylene glycol (Example 3-C) was preferred over the formulation containing only crospovidone (Example 3-A) by 10 of 11 respondents. The same formulation containing crospovidone and polyethylene glycol (Example 3-C) was also preferred over the formulation containing only polyethylene glycol (Example 3-B) by 9 of 11 respondents. These results indicate that significant taste masking effect was achieved when polyvinyl pyrrolidone is used in combination with a high molecular weight polyethylene glycol, and that a significantly lower level of PEG is required for tastemasking in the presence of polyvinyl pyrrolidone than when using PEG alone.

Experiment 4

This example describes the production of a liquid taste masked suspension containing the analgesic acetaminophen.

TABLE 10

Acetaminophen Suspension

| Ingredient | Example 4-A (grams per 100 ml) | Example 4-B (grams per 100 ml) |
| --- | --- | --- |
| Acetaminophen | 5 | 5 |
| Xanthan gum | 0.3 | 0.3 |
| Sucrose | 55 | 55 |
| Sorbitol Solution | 10 | 10 |
| Invert Sugar | 20 | 20 |
| Glycerin | 5 | 5 |
| Crospovidone (Kollidon CL) | 2.5 | 2.5 |
| Polyethylene Glycol 4000 | 0.25 | 0 |
| Sodium Benzoate | 0.2 | 0.2 |
| Sorbitan Monolaurate | 0.05 | 0.05 |
| Disodium Edetate | 0.2 | 0.2 |
| Sucralose | 0.2 | 0.2 |
| Saccharin sodium | 0.13 | 0.13 |
| Coloring | 0.006 | 0.006 |
| Flavoring | 0.3 | 0.3 |
| Citric Acid | 0.1 | 0.1 |
| Sodium Citrate Dihydrate | 0.295 | 0.295 |
| Purified Water | q.s. | q.s. |
| pH | 5–6 | 5–6 |

The acetaminophen suspensions were prepared in the following manner:

Sucrose syrup containing sodium benzoate was prepared. The hot syrup was cooled down to 30□C. The sucrose syrup, sorbitol and invert sugar were blended together to form Phase A, which was then divided into two portions.

A solution of polyethylene glycol (for Example 4-A) in water was prepared. The resulting solution was added to one portion of Phase A. The admixture was stirred for 15 minutes after which sorbitan monolaurate was added directly to the admixture to form Phase B. Crospovidone was dispersed into Phase B. The admixture was stirred for 30 minutes after which acetaminophen was added. The resulting admixture was stirred for one hour to form Phase C.

Xanthan gum was dispersed in glycerin. The resulting dispersion was added to the second portion of Phase A. The admixture was stirred for 15 minutes to form phase D.

An aqueous solution of citric acid and sodium citrate dihydrate was prepared to form Phase E. An aqueous solution of disodium edetate, saccharin sodium and sucralose was prepared to form Phase F.

Phases C, E and F were added to Phase D. The admixture was stirred for one hour and then homogenized in a colloid mill. Color and flavor were added to this homogenized bulk which was stirred for two more hours before adjusting to the desired volume with sugar syrup. The suspensions were allowed to stand for 24 hours before tasting.

Seven respondents were asked to taste 2.5 ml each of Example 4-A and Example 4-B in random order. The respondents were asked to drink water after each medication, and take unsalted crackers between samples to remove traces of the first sample tasted.

All respondents perceived either a sweet aftertaste or no aftertaste for the formulation containing crospovidone and PEG (Example 4-A), while 5 of 7 respondents detected bitter aftertaste in the formulation containing crospovidone only (Example 4-B).

The result shows the significant reduction/elimination of bitterness when high MW polyethylene glycol is used with PVP.

Example 4-A was further compared to Calpol Six Plus (UK, Glaxo Wellcome), a commercial acetaminophen suspension containing the same drug concentration which is relatively good-tasting among the other brands in the market. Seven of seven respondents preferred Example 4-A to Calpol Six Plus. All the respondents perceived bitterness in Calpol Six Plus.

Experiment 5

The effect of the molecular weight of polyethylene glycol on the taste of a liquid suspension containing acetaminophen was determined.

TABLE 11

Acetaminophen Suspension

| Ingredient | Example 5-A (grams per 100 ml) | Example 5-B (grams per 100 ml) | Example 5-C (grams per 100 ml) |
|---|---|---|---|
| Acetaminophen | 5 | 5 | 5 |
| Xanthan gum | 0.3 | 0.3 | 0.3 |
| Sucrose | 55 | 55 | 55 |
| Sorbitol Solution | 10 | 10 | 10 |
| Invert Sugar | 20 | 20 | 20 |
| Glycerin | 5 | 5 | 5 |
| Crospovidone (Kollidon CL-M) | 5 | 5 | 5 |
| Polyethylene Glycol (MW = 4000) | 0.5 | 0 | 0 |
| Polyethylene Glycol (MW = 1450) | 0 | 0.5 | 1 |
| Sodium Benzoate | 0.2 | 0.2 | 0.2 |
| Sorbitan Monolaurate | 0.05 | 0.05 | 0.05 |
| Disodium Edetate | 0.2 | 0.2 | 0.2 |
| Sucralose | 0.2 | 0.2 | 0.2 |
| Saccharin sodium | 0.13 | 0.13 | 0.13 |
| Coloring | 0.006 | 0.006 | 0.006 |
| Flavoring | 0.3 | 0.3 | 0.3 |
| Citric Acid | 0.1 | 0.1 | 0.1 |
| Sodium Citrate Dihydrate | 0.295 | 0.295 | 0.295 |
| Purified Water | q.s. | q.s. | q.s. |
| pH | 5–6 | 5–6 | 5–6 |

The acetaminophen suspensions were prepared in the following manner:

Sucrose syrup containing sodium benzoate was prepared. The hot syrup was cooled down to 30°C. The sucrose syrup, sorbitol and invert sugar were blended together to form Phase A A solution of polyethylene glycol in water was prepared. The resulting solution was added to Phase A. The admixture was stirred for 15 minutes after which sorbitan monolaurate was added directly to the admixture to form Phase B. Crospovidone was dispersed into Phase B. The admixture was stirred for 30 minutes after which acetaminophen was added. The resulting admixture was stirred for one hour to form Phase C.

Xanthan gum was dispersed in glycerin. The resulting dispersion was added to the second portion of Phase C. The admixture was stirred for 15 minutes to form phase D.

An aqueous solution of citric acid and sodium citrate dihydrate was prepared to form Phase E. An aqueous solution of disodium edetate, saccharin sodium and sucralose was prepared to form Phase F.

Phases E and F were added to Phase D. The admixture was stirred for one hour and then homogenized in a colloid mill. Color and flavor were added to this homogenized bulk which was stirred for two more hours before adjusting to the desired volume with sugar syrup.

The viscosity of the samples were determined using a Brookfield Model DV—I+ viscometer using a number 3 spindle at 30 rpm. The samples had the same viscosity.

Two rounds of taste tests were done comparing Example 5-A with Example 5-B, and Example 5-A with Example 5-C, respectively. Ten respondents were asked to taste 2.5 ml of each sample in random order. The respondents were asked to drink water after each medication, and take unsalted crackers between samples to remove traces of the first sample tasted. Each respondent was asked to pick a preference based on reduced bitterness.

Seven out of ten respondents preferred Example 5-A (5% crospovidone +0.5% PEG 4000) over Example 5-B (5% crospovidone +0.5% PEG 1450), and one respondent found no difference between the two products. On the other hand, Example 5-A (5% crospovidone +0.5% PEG 4000) and Example 5-C (5% crospovidone +1% PEG 1450) were equally preferred. Thus, the higher the molecular weight of PEG, the lower the level required for taste masking.

Those ordinarily skilled in the art should be able to run routine experiments to determine the optimum levels of polymer (PVP and/or copovidone) and polyethylene glycol required for achieving maximum taste masking of a given unpleasant-tasting drug.

Experiment 6

This example describes the production of a liquid taste masked suspension containing a high dose of the analgesic acetaminophen.

TABLE 12

Acetaminophen Suspension

| Ingredient | Example 6-A Grams per 100 ml | Example 6-B Grams per 100 ml |
|---|---|---|
| Acetaminophen | 10 | 10 |
| Xanthan gum | 0.3 | 0.3 |
| Sucrose | 54 | 54 |
| Sorbitol Solution | 10 | 10 |
| Invert Sugar | 20 | 20 |
| Glycerin | 5 | 5 |
| Crospovidone (Kollidon CL-M) | 5 | 5 |
| Polyethylene Glycol 4000 | 1 | 0 |
| Sodium Benzoate | 0.2 | 0.2 |
| Sorbitan Monolaurate | 0.05 | 0.05 |
| Disodium Edetate | 0.2 | 0.2 |
| Sucralose | 0.4 | 0.4 |
| Saccharin sodium | 0.26 | 0.26 |
| Coloring | 0.006 | 0.006 |
| Flavoring | 0.4 | 0.4 |

TABLE 12-continued

Acetaminophen Suspension

| Ingredient | Example 6-A Grams per 100 ml | Example 6-B Grams per 100 ml |
| --- | --- | --- |
| Citric Acid | 0.1 | 0.1 |
| Sodium Citrate Dihydrate | 0.295 | 0.295 |
| Purified Water | q.s. | q.s. |
| pH | 5–6 | 5–6 |

The acetaminophen suspension was prepared in the same manner as Experiment 4. The suspensions were allowed to stand for 24 hours before tasting.

Seven respondents were asked to taste 1.0 ml each of Example 6-A and Example 6-B in random order. The respondents were asked to drink water after each medication, and take unsalted crackers between samples to remove traces of the first sample tasted.

All respondents perceived either a sweet aftertaste or no aftertaste for Example 6-A (5% crospovidone +1% PEG 4000), while 7 of 7 respondents detected bitter aftertaste in Example 6-B (5% crospovidone only) illustrating the significant reduction/elimination of bitterness when high MW polyethylene glycol is used with PVP.

A blind taste was conducted on one hundred mothers comparing Example 6-A with Calpol Infant Drops (UK, Glaxo Wellcome) which contains the same drug concentration. Calpol Infant Drops is a commercial acetaminophen suspension that is relatively good tasting among other brands in the market. Seventy four percent of mothers preferred Example 6-A to Calpol Infant Drops, showing the superior taste masking of a formulation containing PVP and high molecular weight PEG.

Experiment 7

This example describes the production of a liquid taste masked syrup containing the expectorant Guaifenesin.

TABLE 13

Guaifenesin Syrup

| Ingredient | Example 7-A Grams per 100 ml | Example 7-B Grams per 100 ml |
| --- | --- | --- |
| Guaifenesin | 2 | 2 |
| Sucrose | 51 | 51 |
| Sorbitol Solution | 30 | 30 |
| Glycerin | 7.5 | 7.5 |
| Povidone (Kollidon K30) | 2.5 | 2.5 |
| Polyethylene Glycol 4000 | 1.25 | 0 |
| Sodium Benzoate | 0.2 | 0.2 |
| Sucralose | 0.1 | 0.1 |
| Flavoring | 0.3 | 0.3 |
| Citric Acid | 3.7 | 3.7 |
| Purified Water | q.s. to 100 mL | q.s. to 100 mL |
| pH | 3–4 | 3–4 |

The Guaifenesin solution was prepared in the following manner:

Sucrose syrup containing sodium benzoate was prepared. The hot syrup was cooled down to 30°C. The sucrose syrup, glycerin and sorbitol were blended together to form Phase A.

An aqueous solution of polyethylene glycol (for Example 7-A) was prepared. An aqueous solution of Guaifenesin was prepared. The solutions were combined and stirred for 15 minutes to form Phase B.

Povidone was dissolved in water. The resulting solution was added to phase A. The admixture was stirred for 15 minutes to form Phase C. Phase B was added to Phase C to form Phase D.

An aqueous solution of citric acid was prepared to form phase E. An aqueous solution of sucralose was prepared to form Phase F. Phases E and F were added to Phase D. The admixture was stirred for one hour and the flavor added. The resulting admixture was stirred for two more hours to achieve homogeneity, and then purified water was added to adjust to the final volume. The syrups were allowed to stand for 24 hours before tasting.

Eleven respondents were asked to taste 1 ml each of Example 7-A and Example 7-B in random order. The respondents were asked to drink water after tasting each sample, and rest between samples taking unsalted crackers to remove traces of the first sample tasted. Each respondent was asked to pick a preference based on reduced bitterness.

Eight out of eleven respondents preferred Example 7-A (2.5% PVP+1.25% PEG 4000) to Example 7-B (2.5% PVP). The result illustrates the significant reduction/elimination of bitterness in syrups when high MW polyethylene glycol is used with PVP.

Experiment 8

This example describes the preparation of Amoxicillin Trihydrate granules for reconstitution with water.

TABLE 14

Amoxicillin Trihydrate Granules

| Ingredient | Example 8-A Grams per 100 mL | Example 8-B Grams per 100 mL |
| --- | --- | --- |
| Amoxicillin Trihydrate | 13 | 13 |
| Sucrose | 45 | 45 |
| Sorbitan Monolaurate | 0.06 | 0.06 |
| Povidone (Kollidon K30) | 2.5 | 2.5 |
| Polyethylene Glycol 4000 | 0.50 | 0 |
| Methylparaben | 0.10 | 0.10 |
| Propylparaben | 0.02 | 0.02 |
| Sodium Citrate Anhydrous | 0.10 | 0.10 |
| Precipitated Silica | 1.2 | 1.2 |
| Color | 0.004 | 0.004 |
| Flavoring | 0.80 | 0.80 |
| Purified Water | q.s. to 100 mL | q.s. to 100 mL |

The Amoxicillin dry powder was prepared by sieving all the excipients prior to use. The screened excipients were premixed for 10 minutes. Amoxicillin Trihydrate was added to the excipient premix. The resulting powders were mixed for another 10 minutes.

The equivalent weight of granules for 100 mL of reconstituted product was weighed and placed into a bottle. Water was then added to the powders to a volume of 100 mL. The powder-water mixture was shaken until a visually homogeneous suspension was obtained.

Example 8-A was compared to Example 8-B. Ten respondents were requested to taste 1 mL of each sample in random order. Each respondent was requested to drink water after each medication, and take unsalted crackers between samples to remove traces of the first sample tasted. Each respondent was asked to pick a preference based on reduced bitterness.

Eight out of ten respondents preferred Example 8-A to Example 8-B, illustrating the significant reduction/elimination of bitterness in extemporaneously prepared liquid suspensions when high MW polyethylene glycol is used with PVP.

Experiment 9

This example describes the preparation of Cloxacillin Sodium granules for reconstitution with water.

TABLE 15

Cloxacillin Sodium Granules

| Ingredient | Example 9-A Grams per 100 mL | Example 9-B Grams per 100 mL |
|---|---|---|
| Cloxacillin | 2.5 | 2.5 |
| Sucrose | 45 | 45 |
| Sorbitan Monolaurate | 0.06 | 0.06 |
| Copolyvidone | 2.5 | 2.5 |
| Polyethylene Glycol 4000 | 1 | 0 |
| Methylparaben | 0.10 | 0.10 |
| Propylparaben | 0.02 | 0.02 |
| Sodium Citrate Anhydrous | 0.10 | 0.10 |
| Precipitated Silica | 1.2 | 1.2 |
| Color | 0.004 | 0.004 |
| Flavoring | 0.80 | 0.80 |
| Purified Water | q.s. to 100 mL | q.s. to 100 mL |

The Cloxacillin dry powder was prepared by sieving all the excipients prior to use.

The screened excipients were premixed for 10 minutes. Cloxacillin Sodium was added to the excipient premix. The resulting powders were mixed for another 10 minutes.

The equivalent weight of granules for 100 mL of reconstituted product was weighed and placed into a bottle. Water was added to the powders to a volume of 100 mL.

The powder-water mixture was shaken until a visually homogeneous suspension was obtained.

Example 9-A was compared to Example 9-B. Eight respondents were requested to taste 1 mL of each sample in random order. Each respondent was requested to drink water after each medication, and take unsalted crackers between samples to remove traces of the first sample. Each respondent was asked to pick a preference based on reduced bitterness.

Seven out of ten respondents preferred Example 9-A to Example 9-B. The result illustrates the significant reduction/ elimination of bitterness in extemporaneously prepared liquid suspensions when high molecular weight polyethylene glycol is used with Copolyvidone.

Experiment 10

This example describes the production of a liquid taste-masked syrup containing the antitussive Dextromethorphan Hydrobromide.

TABLE 16

Dextromethorphan Hydrobromide Syrup

| Ingredient | grams per 100 ml |
|---|---|
| Dextromethorphan Hydrobromide | 0.3 |
| Sucrose | 60 |
| Povidone (Kollidon K25) | 2.5 |
| Polyethylene Glycol 6000 | 0.25 |
| Sodium Benzoate | 0.2 |
| Sucralose | 0.2 |
| Saccharin sodium | 0.13 |
| Flavoring | 0.3 |
| Citric Acid | 0.64 |
| Sodium Citrate Dihydrate | 2.66 |
| Purified Water | q.s. to 100 mL |
| pH | 4.5–5.5 |

The Dextromethorphan Hydrobromide syrup was prepared in the following manner:

Sucrose syrup containing sodium benzoate was prepared. The hot syrup was cooled down to 30°C. to form Phase A.

A solution of polyethylene glycol in water was prepared. Dextromethorphan Hydrobromide was dissolved in this solution. The admixture was stirred for 15 minutes to form Phase B. Phase B was then added to Phase A and stirred for 15 minutes to form Phase C. Povidone was added directly into Phase C and stirred for one hour to form Phase D.

An aqueous solution of citric acid and sodium citrate dihydrate was prepared to form phase E. An aqueous solution of saccharin sodium and sucralose was prepared to form Phase F. Phases E and F were added to Phase D. The admixture was stirred for one hour and the flavor added. The resulting admixture was stirred for two more hours to achieve homogeneity, and then purified water was added to adjust to the final volume.

The formulation has an acceptable taste with no bitterness.

Experiment 11

This example describes the production of a liquid taste masked syrup containing the antihistamine Diphenhydramine Hydrochloride.

TABLE 17

Diphenhydramine Hydrochloride Syrup

| Ingredient | grams per 100 ml |
|---|---|
| Diphenhydramine Hydrochloride | 0.3 |
| Sorbitol | 40 |
| Glycerin | 30 |
| Povidone (Kollidon K25) | 5.0 |
| Polyethylene Glycol 8000 | 2.25 |
| Sodium Benzoate | 0.2 |
| Sucralose | 0.2 |
| Saccharin sodium | 0.13 |
| Flavoring | 0.3 |
| Citric Acid | 0.64 |
| Sodium Citrate Dihydrate | 2.66 |
| Purified Water | q.s. to 100 mL |
| pH | 4.5–5.5 |

The Diphenhydramine Hydrochloride syrup was prepared in the following manner:

The sorbitol and glycerin were blended together to form Phase A.

A solution of polyethylene glycol in water was prepared. Diphenhydramine Hydrochloride was dissolved in this solution. The admixture was stirred for 15 minutes to form Phase B. Phase B was then added to Phase A and stirred for 15 minutes to form Phase C. Povidone was added directly into Phase C and stirred for one hour to form Phase D.

An aqueous solution of citric acid and sodium citrate dihydrate was prepared to form phase E. An aqueous solution of saccharin sodium and sucralose was prepared to form Phase F. Phases E and F were added to Phase D. The admixture was stirred for one hour and the flavor added. The resulting admixture was stirred for two more hours to achieve homogeneity, and then purified water was added to adjust to the final volume.

The formulation has an acceptable taste with no bitterness.

Experiment 12

This example describes the production of a liquid taste masked syrup containing the antihistamine Brompheniramine Maleate.

TABLE 18

Brompheniramine Maleate Syrup

| Ingredient | grams per 100 ml |
|---|---|
| Brompheniramine maleate | 0.08 |
| Sorbitol Solution | 40 |
| Glycerin | 30 |
| Povidone (Kollidon K25) | 2.5 |
| Polyethylene Glycol 3350 | 2.25 |
| Sodium Benzoate | 0.2 |
| Sucralose | 0.2 |
| Saccharin sodium | 0.13 |
| Flavoring | 0.3 |
| Citric Acid | 0.05 |
| Purified Water | q.s. to 100 mL |
| pH | 3–4 |

The Brompheniramine Maleate syrup was prepared in the following manner:

The sorbitol and glycerin were blended together to form Phase A.

A solution of polyethylene glycol in water was prepared. Brompheniramine maleate was dissolved in this solution. The admixture was stirred for 15 minutes to form Phase B. Phase B was then added to Phase A and stirred for 15 min to form Phase C. Povidone was added directly into Phase C and stirred for one hour to form Phase D.

An aqueous solution of citric acid was prepared to form phase E. An aqueous solution of saccharin sodium and sucralose was prepared to form Phase F. Phases E and F were added to Phase D. The admixture was stirred for one hour and the flavor added. The resulting admixture was stirred for two more hours to achieve homogeneity, and then purified water was added to adjust to the final volume.

The formulation has an acceptable taste with no bitterness.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A taste-masked liquid pharmaceutical composition or an extemporaneously prepared liquid pharmaceutical composition, comprising:
   at least one unpleasant tasting drug;
   polyethylene glycol of molecular weight at least 900, and polyvinyl pyrrolidone and/or copolyvidone,
   wherein a final form of said taste-masked pharmaceutical composition administered to a patient is a liquid, said liquid having a substantially non-bitter taste.

2. The method according to claim 1, wherein said liquid pharmaceutical composition has a pH from about 2.5 to about 8.

3. The liquid pharmaceutical composition according to claim 1, wherein the unpleasant drug is an aromatic compound with a hydrophilic group(s) that can form hydrogen bonds such as hydroxyl, carboxylic or amine groups.

4. The liquid pharmaceutical composition according to claim 1 wherein the unpleasant drug is present at about 0.02 to about 15 percent by weight.

5. The liquid pharmaceutical composition according to claim 1, wherein the amount of polyethylene glycol is from about 0.05 to about 10 weight percent.

6. The liquid pharmaceutical composition according to claim 5, wherein the amount of polyethylene glycol is from about 0.1 to about 5 weight percent.

7. The liquid pharmaceutical composition according to claim 1, wherein said polyethylene glycol is of molecular weight of from about 2000 to about 8000.

8. The liquid pharmaceutical composition according to claim 1, wherein the polyvinyl pyrrolidone and/or copolyvidone is present at about 0.1 to about 30 weight percent.

9. The liquid pharmaceutical composition according to claim 8, wherein the polyvinyl pyrrolidone and/or copolyvidone is present at about 1 to about 7 weight percent.

10. The liquid pharmaceutical compositions according to claim 1, further comprising a sweetening agent and/or a viscosity building agent.

11. The liquid pharmaceutical composition according to claim 10, wherein the said sweetening agent is selected from the group consisting of sugar, invert sugar, glucose, fructose, sorbitol, mannitol, xylitol, a high intensity artificial sweetener, a dipeptide sweetener, and combinations thereof.

12. The liquid pharmaceutical composition according to claim 10, wherein said sweetening agent is present at about 30 to about 90 weight percent.

13. The liquid pharmaceutical composition according to claim 10, wherein the said viscosity-building agent is selected from the group consisting of glycerin, xanthan gum, carrageenan, tragacanth, guar gum, pectin, carboxymethylcellulose, hydroxypropyl methylcellulose, methylcellulose, microcrystalline cellulose and carboxymethylcellulose blends, and mixtures thereof.

14. The liquid pharmaceutical composition according to claim 10, wherein said viscosity building agent is present in an amount from about 0.1 to about 3 weight percent.

15. The liquid pharmaceutical composition according to claim 1, wherein said composition is used to treat fever, infection, headache, pain, inflammation, excess mucus or phlegm, coughing, allergies, allergic diseases, nausea, vomiting, and motion sickness.

16. The liquid pharmaceutical composition according to claim 15, wherein said unpleasant tasting drug is selected from the group consisting of an analgesic, an anti-inflammatory drug, an antihistamine, a decongestant, anti-infective, a mucolytic, an antitussive, an expectorant, and combinations thereof.

17. The liquid pharmaceutical composition according to claim 16, wherein said analgesic or said anti-inflammatory drug is selected from the group consisting of acetaminophen, ibuprofen, naproxen, mefenamic acid, ketoprofen, celecoxib, rofecoxib, and tramadol, and combinations thereof.

18. The liquid pharmaceutical composition according to claim 16, wherein said antihistamine is selected from the group consisting of loratadine, descarboethoxyloratadine, diphenhydramine, brompheniramine, chlorpheniramine, terfenadine, cetirizine, and combinations thereof.

19. The liquid pharmaceutical composition according to claim 16, wherein said decongestant is selected from phenylpropanolamine, pseudoephedrine, phenylephrine, and combinations thereof.

20. The liquid pharmaceutical composition according to claim 16, wherein said anti-infective is selected from amoxicillin, ampicillin, cloxacillin, flucloxacillin, penicillin, cephalexin, and combinations thereof.

21. The liquid pharmaceutical composition according to claim 16, wherein said mucolytic is selected from the group consisting of ambroxol, carbocisteine, and bromhexine, and combinations thereof.

22. The liquid pharmaceutical composition according to claim 16, herein said antitussive or said expectorant is selected from the group consisting of caramiphen, dextromethrophan hydrobromide, codeine phosphate, codeine sulfate, guaifenesin, and combinations thereof.

23. The liquid pharmaceutical composition according to claim 22, wherein said guaifenesin is present in an amount of about 1 to about 5 weight percent.

24. The liquid pharmaceutical composition according to claim 23, further comprising at least one additional drug selected from the group consisting of a bronchodilator, a mucolytic, an antitussive, and combinations thereof.

25. The liquid pharmaceutical composition according to claim 24, wherein said bronchodilator is selected from the group consisting of salbutamol, terbutaline, theophylline, and combinations thereof.

26. The liquid pharmaceutical composition according to claim 24, wherein said antitussive is selected from the group consisting of caramiphen, dextromethrophan hydrobromide, codeine phosphate, codeine sulfate, and combinations thereof.

27. The liquid pharmaceutical composition according to claim 24, wherein said mucolytic is selected from the group consisting of ambroxol, carbocisteine, and bromhexine, and combinations thereof.

28. The liquid pharmaceutical composition according to claim 17, wherein said acetaminophen is present in an amount of about 1 to about 10 weight percent.

29. The liquid pharmaceutical composition according to claim 28, further comprising at least one additional drug selected from the group consisting of an analgesic, an anti-inflammatory drug, an antihistamine, a decongestant, an antitussive, an expectorant, a mucolytic, and combinations thereof.

30. The liquid pharmaceutical composition according to claim 29 wherein said analgesic or said anti-inflammatory agent is selected from the group consisting ibuprofen, naproxen, mefenamic acid, ketoprofen, celecoxib, rofecoxib, tramadol, and combinations thereof.

31. The liquid pharmaceutical composition according to claim 29, wherein said antihistamine is selected from the group consisting of loratadine, descarboethoxyloratadine, diphenhydramine, brompheniramine, chlorpheniramine, terfenadine, cetirizine, and combinations thereof.

32. The liquid pharmaceutical composition according to claim 29, wherein the decongestant is selected from the group consisting of phenylpropanolamine, pseudoephedrine, phenylephrine, and combinations thereof.

33. The liquid pharmaceutical composition according to claim 29, wherein said antitussive or said expectorant is selected from the group consisting of caramiphen, dextromethrophan hydrobromide, codeine phosphate, codeine sulfate, guaifenesin, and combinations thereof.

34. The liquid pharmaceutical composition according to claim 29, wherein said mucolytic is selected from the group consisting of ambroxol, carbocisteine, and bromhexine, and combinations thereof.

35. A liquid pharmaceutical composition comprising:
    5 g acetaminophen, 0.3 g xanthan gum, 55 g sucrose, 10 g 70% sorbitol solution, 20 g invert sugar, 5 g glycerin, 2.5 to 5 g crospovidone, 0 to 2.5 g polyethylene glycol with an average molecular weight between 1000 to 4000, 0.2 g sodium benzoate, 0.05 g sorbitan monolaurate, 0.2 g edetate disodium, 0.2 g sucralose, 0.13 g saccharin sodium, 0 to 0.006 g FD&C or D&C color, 0.2 to 0.4 g flavor, water to a volume of 100 mL, citric acid-sodium citrate dihydrate to a pH of 5 to 6.

36. A liquid pharmaceutical composition comprising:
    10 g acetaminophen, 0.3 g xanthan gum, 54 g sucrose, 10 g 70% sorbitol solution, 20 g invert sugar, 5 g glycerin, 5 to 10 g crospovidone, 0 to about 1 g polyethylene glycol with an average molecular weight between 1000 to 4000, 0.2 g sodium benzoate, 0.05 g sorbitan monolaurate, 0.2 g edetate disodium, 0.4 g sucralose, 0.26 g saccharin sodium, 0 to 0.006 g FD&C or D&C color, 0.2 to 0.4 g flavor, water to a volume of 100 mL, citric acid-sodium citrate dihydrate to a pH of 5 to 6.

37. A liquid pharmaceutical composition comprising:
    2 to 4 g guaifenesin, 51 g sucrose, 30 g 70% sorbitol solution, 7.5 g glycerin, 2.5 g to 5 g povidone, 0 to 1.5 g polyethylene glycol with an average molecular weight between 1000 to 4000, 0.2 g sodium benzoate, 0.1 g sucralose, from about 0.2 to about 0.4 g flavor, water to a volume of 100 mL, citric acid to a pH of 3 to 4.

38. A liquid pharmaceutical composition comprising:
    0.3 g dextromethorphan hydrobromide, 60 g sucrose, 20 g invert sugar, 2.5 g to 5g povidone, from about 0 to 1 g polyethylene glycol with an average molecular weight between 1000 to 6000, 0.2 g sodium benzoate, 0.2 g sucralose. 0.13 g saccharin sodium, 0.2 to about 0.4 g flavor, water to a volume of 100 mL, citric acid-sodium citrate dihydrate to a pH of 4.5 to 5.5.

39. A liquid pharmaceutical composition comprising:
    0.3 g diphenhydramine hydrochloride, 40 g 70% sorbitol solution, 30 g glycerin, 2.5 g to 5 g povidone, 0 to 2.25 g polyethylene glycol with an average molecular weight between 1000 to 8000, 0.2 g sodium benzoate, 0.2 g sucralose. 0.13 g saccharin sodium, 0.2 to 0.4 g flavor, water to a volume of 100 mL, citric acid-sodium citrate dihydrate to a pH of 4.5 to 5.5.

40. A liquid pharmaceutical composition comprising:
    0.08 g brompheniramine maleate, 40 g 70% sorbitol solution, 30 g glycerin, 2.5 g to 5 g povidone, 0 to 2.25 g polyethylene glycol with an average molecular weight between 1000 to 8000, 0.2 g sodium benzoate, 0.2 g sucralose. 0.13 g saccharin sodium, 0.2 to 0.4 g flavor, water to a volume of 100 mL, citric acid-sodium citrate dihydrate to a pH of 3 to 4.

41. A ready-to-use powder or granules for reconstitution wherein after reconstitution to 100 mL with water, the liquid pharmaceutical composition comprises:
    3.25 to 13 g amoxicillin trihydrate, 45 g sucrose, 0.06 g sorbitan monolaurate, 0.5 to 2.5 g povidone and/or copolyvidone, 0.1 to about 0.5 g polyethylene glycol with an average molecular weight between 1000 to 8000, 0.10 g methylparaben, 0.02 propylparaben, 0 to 0.004 g FD&C or D&C color, 0.20 to 1 g flavor, 1.2 g precipitated silica, and sodium citrate to pH 4–6.

42. A ready-to-use powder or granules for reconstitution wherein after reconstitution to 100 mL with water, the liquid pharmaceutical composition comprises:
    2 to 10 g cloxacillin sodium, 45 g sucrose, 0.06 g sorbitan monolaurate, 0.5 to 2.5 g povidone and/or copolyvidone, 0.1 to about 0.5 g polyethylene glycol with an average molecular weight between 1000 to 8000, 0.10 g methylparaben, 0.02 propylparaben, 0 to 0.004 g FD&C or D&C color, 0.20 to 1 g flavor, 1.2 g precipitated silica, and sodium citrate to pH 4–6.

43. A method for preparing a taste-masked liquid pharmaceutical composition, comprising combining:

at least one unpleasant-tasting drug;

polyethylene glycol with a molecular weight of at least 900;

polyvinyl pyrrolidone and/or a copolyvidone; and an aqueous liquid excipient base, and wherein a final form of said taste-masked pharmaceutical composition administered to a patient is a liquid, said liquid having a substantially non-bitter taste.

44. The method according to claim 43, wherein said polyethylene glycol has an average molecular weight of from about 2000 to about 8000.

45. The method according to claim 43, wherein said polyethylene glycol has an average molecular weight of from about 4000 to about 6000.

46. The method according to claim 43, wherein said liquid pharmaceutical composition further comprises one or more additives selected from the group consisting of sweetening agents, flavors, colorants, antioxidants, chelating agents, viscosity-building agents, surfactants, pH modifiers, bulking agents, acidifiers, cosolvents, anticaking agents, and mixtures thereof.

* * * * *